(12) United States Patent
Deák et al.

(10) Patent No.: US 6,563,019 B1
(45) Date of Patent: May 13, 2003

(54) OXIDATIVE STRESS RESISTANCE GENE

(75) Inventors: Mària Deák, Szeged (HU); Dénes Dudits, Szeged (HU); Károlyne Török, Szeged-Tape (HU); Laszlo Sass, Szeged (HU); Barna Balázs, Budapest (HU); Zoltán Király, Budapest (HU)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/418,830

(22) Filed: Oct. 15, 1999

Related U.S. Application Data

(63) Continuation of application No. PCT/GB98/01108, filed on Apr. 16, 1998.

(30) Foreign Application Priority Data

Sep. 22, 1997 (HU) .............................................. 9700762
Apr. 16, 1997 (HU) .............................................. 9700762
Mar. 9, 1998 (HU) .............................................. 9700762

(51) Int. Cl.$^7$ ........................ C12N 15/09; C12N 15/29; C12N 15/82; A01H 5/00

(52) U.S. Cl. ........................ 800/279; 800/278; 800/298; 800/295; 800/289; 435/69.1; 435/419; 435/418; 435/468; 536/23.1; 536/23.6

(58) Field of Search ................................ 800/278, 298, 800/295, 289, 279; 435/69.1, 419, 418, 468; 536/23.6, 23.1

(56) References Cited

FOREIGN PATENT DOCUMENTS

| JP | 9-140384 | 6/1997 |
|---|---|---|
| JP | 9-201190 | 8/1997 |
| WO | WO 96/31612 | 10/1996 |

OTHER PUBLICATIONS

Linthorst et al "Constitutive Expression of Pathogenesis–Related Proteins PR–1, GRP and PR–S in Tobacco Has No Effect on Virus Infection", 1989, The Plant Cell, vol. 1 pp. 285–291.*
Mitra et al Expression of a Human Lactoferrin cDNA in Tobacco Cells Produces Antibacterial Protein(s), 1994 Plant Physiol. vol. 106 pp. 977–981.*
Mitra, M et al "Expression of a human lactoferrin cDNA in tobacco cells produces antibacterial protein(s)", Plant Physiol, 106, pp977–981 (1994) XP–002048441.
Wuytswinkel, O et al "Iron homeostasis alteration in transgenic tobacco overexpressing ferritin", The Plant Journal, 17(1), pp93–97 (1998).
Bohnert, H et al "Strategies for engineering water–stress tolerance in plants", Tibtech 14 pp89–97 (1996).
Allen, R "Dissection of oxidative street tolerance using transgenic plants", Plant Physiol, 107 pp1049–1054 (1995) XP–002072721.

Spence, M et al "The structure of a phaseolus vulgaris cDNA encoding the iron storage protein ferritin", Plant Molecular Biology, 17 pp499–504 (1991) XP–002072722.
Hammond–Kosack, K et al "Resistance gene–dependent plant defense responses", The Plant Cell 8 pp1773–1791 (1996) XP–002049471.
Goto, F et al "Iron accumulation in tobacco plants expressing soyabean ferritin gene", Transgenic Research 7, pp173–180 (1998).
Lobreaux, S et al "Iron induces ferritin synthesis in maize plantlets" Plant Molecular Biology 19 pp563–572 (1992) XP–002072723.
Fobis–Loisy, I et al "Structure and differential expression of two maize ferritin genes in response to iron and abscisic acid" Eur J. Biochem 231 pp609–619 (1995) XP–002072718.
Lescure, A et al "Ferritin gene transcription is regulated by iron in soybean cell cultures" Proc. Natl.
Acad. Sci. USA 88, pp8222–8226 (1991) XP–002072719.
Gaymard, F et al "Characterization of a ferritin mRNA from Arabidopsis thaliana accumulated in response to iron through an oxidative pathway independent of abscisic acid", Biochem J 318 pp67–73 (1996) XP–002072717.
Roxas, V et al "Overexpression of glutathione S–transferase/ glutathione peroxidase enhances the growth of transgenic tobacco seedlings during stress" Nature Biotechnology 15 (1997).
Laulhere, J et al "Dynamic equilibria in iron uptake and release by ferritin" BioMetals 9 pp303–309 (1995).
Joshi, J et al "Ferritin: an iron storage protein with diverse functions" BioFactors 1 pp207–212 (1988).
Caris, C et al "Metabolization of iron by plant cells using O–Trensox, a high affinity abiotic iron–chelating agent" Biochem, J. 312 pp879–885 (1995).
Kurtz, D et al "Structural similarity and functional diversity in diiron–oxo proteins" JBIC 2 pp159–167 (1997).

(List continued on next page.)

Primary Examiner—Phuong T. Bui
Assistant Examiner—Medina A. Ibrahim
(74) Attorney, Agent, or Firm—Nixon & Vanderhye

(57) ABSTRACT

The invention relates to plants, especially transgenic plants, plant parts and plant cells overproducing an iron binding protein (e.g., ferritin) and having an enhanced resistance against a wide range of abiotic and biotic oxidative stress conditions (e.g., against treatment with paraquat or fusaric acid and against viral, bacterial or fungal infections). The invention also comprises nucleic acid sequences encoding an alfalfa ferritin or functional variants thereof and the use of such sequences for rendering plants resistant against oxidative stress conditions. The invention is useful for reducing environmental damages of crops caused by a wide variety of stress conditions.

11 Claims, 13 Drawing Sheets

OTHER PUBLICATIONS

Hirling, H et al "Expression of active iron regulatory factor from a fell–length human cDNA by in vitro transcription/translation" Nucleic Acids Research 20(1) pp33–39 (1992).

Harrison, P et al "The ferritins: molecular properties, iron storage function and cellular regulation" Biochimica et Biophysia Acta 1275 pp161–203 (1996).

Lobrèaux S et al "Induction of ferritin synthesis in maize leaves by an iron–mediated oxidative stress" The Plant Journal 8(3) pp443–449 (1995).

Boyer, R et al "Reduction and release of ferritin iron by plant phenolics" Journal of Inorganic Biochemistry 32 pp171–181 (1998).

Luo, M et al "Characterization of a gene family encoding abscisic acid–and environmental stressinducible proteins of Alfalfa" The Journal of Biological Chemistry 267(5) pp15367–15374 (1992).

Derwent abstract XP–002072725.

Derwent abstract XP–002072724.

XP–002094163.

Food Chemical News pp 34–37 (Jan. 1994).

Kon S "Decontrolled iron: an ultimate carcinogen and toxicant: an hypothesis" Biological Autoxidation.

* cited by examiner

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     |     |     |     |     |     |     |     |     |     |     |     | Met | Ala | Leu |
| 1   | CTC | AAT | TTT | CTC | AAC | GAC | CCT | TTT | TGT | TAT | TCT | TCT | TTA | ATG | GCT | CTT | 48 |
| 4   | Ser | Ala | Ser | Lys | Val | Ser | Ile | Phe | Ser | Pro | Ile | Val | Gly | His | | | 19 |
| 49  | TCA | GCT | TCC | AAA | GTT | TCG | ATC | TTT | TCA | CCA | ATC | GTG | GGT | CAT | | | 96 |
| 20  | Phe | Ser | Lys | Asn | Thr | Thr | Phe | Ser | Ser | Leu | Asn | Leu | Pro | Met | Asp | Gly | 35 |
| 97  | TTC | TCA | AAA | AAC | ACC | ACT | TTT | TCT | TCT | TTG | AAT | CTT | CCT | ATG | GAT | GGT | 144 |
| 36  | Asp | Lys | Arg | Lys | Asn | Val | Lys | Val | His | Ala | Ala | Ala | Asn | Ala | Pro | | 51 |
| 145 | GAT | AAG | AGG | AAG | AAC | GTG | AAG | GTT | CAT | GCT | GCT | GCT | AAT | GCA | CCA | | 192 |
| 52  | Thr | Ala | Leu | Thr | Gly | Val | Ile | Phe | Glu | Pro | Phe | Glu | Glu | Val | Lys | Lys | 67 |
| 193 | ACG | GCA | TTA | ACA | GGT | GTT | ATC | TTT | GAA | CCG | TTT | GAA | GAA | GTC | AAG | AAA | 240 |
| 68  | Asp | Val | Leu | Ala | Val | Pro | Ile | Ala | His | Asn | Val | Ser | Leu | Ala | Arg | Gln | 83 |
| 241 | GAT | GTT | CTT | GCT | GTT | CCT | ATT | GCT | CAT | AAT | GTT | TCC | TTG | GCT | CGT | CAG | 288 |
| 84  | Asn | Tyr | Gln | Asp | Glu | Val | Glu | Ser | Ala | Ile | Asn | Glu | Gln | Ile | Asn | Val | 99 |
| 289 | AAT | TAT | CAA | GAT | GAA | GTT | GAA | TCT | GCT | ATC | AAT | GAA | CAG | ATT | AAT | GTG | 336 |

Fig. 1A

| 100 | Glu | Tyr | Asn | Val | Ser | Tyr | Val | Tyr | His | Ser | Leu | Phe | Ala | Tyr | Phe | Asp | 115 |
| --- | --- | --- | --- | --- | --- | --- | --- | --- | --- | --- | --- | --- | --- | --- | --- | --- | --- |
| 337 | GAA | TAC | AAT | GTT | TCC | TAT | GTG | TAC | CAC | TCT | TTG | TTT | GCA | TAC | TTT | GAC | 384 |
| 116 | Arg | Asp | Asn | Val | Ala | Leu | Lys | Gly | Leu | Ala | Lys | Phe | Lys | Glu | Ser | | 131 |
| 385 | AGA | GAC | AAC | GTT | GCT | CTC | AAG | GGA | CTT | GCC | AAG | TTC | AAG | GAA | TCT | | 432 |
| 132 | Ser | Glu | Glu | Arg | Glu | His | Ala | Glu | Lys | Leu | Met | Lys | Tyr | Gln | Asn | | 147 |
| 433 | AGT | GAG | GAA | AGA | GAA | CAT | GCT | GAG | AAG | CTC | ATG | AAA | TAC | CAG | AAT | | 480 |
| 148 | Ile | Arg | Gly | Gly | Arg | Val | Val | Leu | His | Pro | Ile | Val | Ser | Pro | Ser | | 163 |
| 481 | ATT | CGT | GGT | GGA | AGA | GTG | GTG | CTG | CAC | CCT | ATT | GTG | AGC | CCC | TCG | | 528 |
| 164 | Glu | Phe | Asp | His | Ala | Glu | Lys | Gly | Asp | Ala | Leu | Tyr | Ala | Met | Glu | Leu | 179 |
| 529 | GAA | TTT | GAT | CAT | GCA | GAA | AAG | GGA | GAT | GCA | TTA | TAT | GCC | ATG | GAA | TTG | 576 |
| 180 | Ala | Leu | Ser | Leu | Glu | Lys | Leu | Val | Asn | Glu | Lys | Leu | Leu | Asn | Val | His | 195 |
| 577 | GCT | CTG | TCT | TTG | GAG | AAG | TTA | GTA | AAT | GAG | AAA | CTT | CTG | AAT | GTT | CAC | 624 |
| 196 | Ser | Val | Ala | Asp | Arg | Asn | Asn | Asp | Pro | Gln | Leu | Ala | Asn | Phe | Ile | Glu | 211 |
| 625 | AGT | GTG | GCT | GAT | CGT | AAC | AAT | GAT | CCT | CAA | TTG | GCA | AAT | TTC | ATC | GAG | 672 |

```
212  Ser Glu Phe Leu Val Glu Gln Val Glu Ser Ile Lys Lys Ile Ser Glu        227
673  AGC GAG TTT TTG GTA GAG CAG GTT GAA TCA ATT AAG AAG ATA TCA GAG        720

228  Tyr Val Thr Gln Leu Arg Leu Val Gly Lys Gly His Gly Val Trp His        243
721  TAT GTG ACT CAA CTG AGA TTA GTT GGA AAG GGT CAC GGT GTG TGG CAC        768

244  Phe Asp Gln Thr Leu Leu His ***                                       250
769  TTT GAT CAG ACT CTT CAT TGA TTA ATA TGA TGT TTG ATC TTG AAG            816

817  AAG CTA CGT GTT TTT GTT TAG AAC GTA GAA GCT GTG TGA ATG               864

865  TAT TCT CCT AGG TAA TTT GAA TTA TGT GTA GAG CCA TAA TAA CTG           912

913  GTT GCT TAG TAA GAA TTA GAA GAC TTG GAG CCA TAA TAA CTG                960

961  TTT GTA GCT TGC AGA AAT TAT TTT GTT AGA AAT GAA AAT GAG CTT GGC       1008

1009 TAT TAC TAC TAA AAA AAA AAA A                                         1036
```

```
         1          10         20         30         40         50         60
Msfer1   LTGVIFEPFEEVKKDVLAVPIAHNVSLARQNYQDEVESAINEQINVEYNVSYVYHSLFAY
         ************************    *    ****** ******************
Peafer   LTGVIFEPFEEVKKDYLAVPSVPLVSLARQNFADECESVINEQINVEYNASYVYHSLFAY
                       ::    *      ****:: :*    **  ** ****   *
HuHfer              MTTASTSQV...RQNYHQDSEAAINRQINLELYASYVVLSMSYY
                                 ****  :  : .*** **: *** :: *  *:
HoLfer                    SSQI...RQNYSTEVEAAVNRLVNLYLRASYTYLSLGFY
```

Fig. 2A

```
                  70        80        90       100       110       120
Msfer1   FDRDNVALKGLAKFFKESSEEEREHAEKLMKYQNIRGGRVVLHPIVSPPSEFDHAEKGDA
         ***** *:***** ***** * ***:******************** * ****: ****
Peafer   FDRDNVALKGFAKFFKESSEEHREHAEKLMKYQNTRGGRVVLHPIKDVPSEFEHVEKGDA
         ***::*** *  ***   ***::****** ****  *:*** ***  *   ** 
HuHfer   FDRDDVALKNFAKYFLHQSHEEREHAEKLMKLQNQRGGRIFLQDIKKPDCD.....DWESG
              :**    *     ::      *  **     *:    **    *
HoLfer   FDRDDVALEGVCHFFRELAEEKREGAERLLKMQNQRGGRALFQDLQKPSQD.....EWGTT
```

Fig. 2B

```
                  130              140             150            160            170           180
Msfer1    LYAMELALSLEKLVNEKLLNVHSVADRNNDPQLANFIESEFLVEQVESIKKISEYVTQLR
          ************* **** ******* *****       **  :*   ***** ****** ***
Peafer    LYAMELALSLEKLTNEKLLNVHSVAERNNDLEMTHFIEGEYLAEQVEAIKKISEYVAQLR
          * **** **  **: **: **  *** ***  :  *  ** ****  *  ..  :.**
HuHfer    LNAMECALHLEKNVNQSLLELHKLATDKNDPHLCDFIETHYLNEQVKAIKELGDHVTNLR
          *:;**   * **:  *  ***:;:**   :;**** **
HoLfer    LDAMKAAIVLEKSLNQALLDLHALGSAQADPHLCDFLESHFLDEEVKLIKKMGDHLTNIQ
```

Fig. 2C

```
                190       197
Msfer1   LVG...KGHGVWHFDQTLLH
           **   ********** ***
Peafer   RVG...KGHGVWHFDQRLLLHGVHGA
           *            *    **         *
HuHfer   KMGAPESGLAEYLFDKHTLGDSDNES
          ::   :  ** *****:.    **
HoLfer   RLVGSQAGLGEYLFERLTLKHD
```

Fig. 2D

SEQUENCE LISTING

```
<160> NUMBER OF SEQ ID NOS:  6

<210> SEQ ID NO 1
<211> LENGTH: 1036
<212> TYPE: DNA
<213> ORGANISM: Medicago sativa
<220> FEATURE:
<221> NAME/KEY: transit_peptide
<222> LOCATION: (40)..(201)
<221> NAME/KEY: CDS
<222> LOCATION: (40)..(789)

<400> SEQUENCE: 1
ctcaattttc tcaacgaccc tttttgttat tcttcttta atg gct ctt tca gct          54
                                             Met Ala Leu Ser Ala
                                               1               5 tcc aaa gtt tcg atc ttt tca cca tca cct atc gtg ggt cat ttc tca        102
Ser Lys Val Ser Ile Phe Ser Pro Ser Pro Ile Val Gly His Phe Ser
                 10                  15                  20 aaa aac acc act ttt tct tct ttg aat ctt cct atg gat ggt gat aag        150
Lys Asn Thr Thr Phe Ser Ser Leu Asn Leu Pro Met Asp Gly Asp Lys
             25                  30                  35 agg aag aac gtg aag gtt cat gct gct gct gca aat gca cca acg gca        198
Arg Lys Asn Val Lys Val His Ala Ala Ala Ala Asn Ala Pro Thr Ala
         40                  45                  50 tta aca ggt gtt atc ttt gaa ccg ttt gaa gaa gtc aag aaa gat gtt        246
Leu Thr Gly Val Ile Phe Glu Pro Phe Glu Glu Val Lys Lys Asp Val
     55                  60                  65 ctt gct gtt cct att gct cat aat gtt tcc ttg gct cgt cag aat tat        294
Leu Ala Val Pro Ile Ala His Asn Val Ser Leu Ala Arg Gln Asn Tyr
 70                  75                  80                  85 caa gat gaa gtt gaa tct gct atc aat gaa cag att aat gtg gaa tac        342
Gln Asp Glu Val Glu Ser Ala Ile Asn Glu Gln Ile Asn Val Glu Tyr
                 90                  95                 100 aat gtt tcc tat gtg tac cac tct ttg ttt gca tac ttt gac aga gac        390
Asn Val Ser Tyr Val Tyr His Ser Leu Phe Ala Tyr Phe Asp Arg Asp
             105                 110                 115 aac gtt gct ctc aag gga ctt gcc aag ttc ttt aag gaa tct agt gag        438
Asn Val Ala Leu Lys Gly Leu Ala Lys Phe Phe Lys Glu Ser Ser Glu
         120                 125                 130 gaa gaa aga gag cat gct gag aag ctc atg aaa tac cag aat att cgt        486
Glu Glu Arg Glu His Ala Glu Lys Leu Met Lys Tyr Gln Asn Ile Arg
     135                 140                 145 ggt gga aga gtg gtg ctg cac cct att gtg agc cct ccc tcg gaa ttt        534
Gly Gly Arg Val Val Leu His Pro Ile Val Ser Pro Pro Ser Glu Phe
150                 155                 160                 165 gat cat gca gaa aag gga gat gca tta tat gcc atg gaa ttg gct ctg        582
Asp His Ala Glu Lys Gly Asp Ala Leu Tyr Ala Met Glu Leu Ala Leu
                 170                 175                 180 tct ttg gag aag tta gta aat gag aaa ctt ctg aat gtt cac agt gtg        630
Ser Leu Glu Lys Leu Val Asn Glu Lys Leu Leu Asn Val His Ser Val
             185                 190                 195 gct gat cgt aac aat gat cct caa ttg gca aat ttc atc gag agc gag        678
Ala Asp Arg Asn Asn Asp Pro Gln Leu Ala Asn Phe Ile Glu Ser Glu
         200                 205                 210 ttt ttg gta gag cag gtt gaa tca att aag aag ata tca gag tat gtg        726
```

```
Phe Leu Val Glu Gln Val Glu Ser Ile Lys Lys Ile Ser Glu Tyr Val
    215                 220                 225 act caa ctg aga tta gtt gga aag ggt cac ggt gtg tgg cac ttt gat      774
Thr Gln Leu Arg Leu Val Gly Lys Gly His Gly Val Trp His Phe Asp
230                 235                 240                 245 cag act ctt ctc cat tgattaatat gatgtttgat cttgaagaag ctacgtgttg      829
Gln Thr Leu Leu His
            250 tttttacatt actggaatag tgaataaatg aaatgtattc tcctaggtaa ttttagaacg    889 tagaagctgt gtgtaatatt ttagttgctt agtaagaatt atgtgtagaa gacttggagc    949 cataataact gtttgtagct tgcagaaatt attttgttag aaatgaaaat gagcttggct   1009 attactacta aaaaaaaaaa aaaaaaa                                       1036

<210> SEQ ID NO 2
<211> LENGTH: 250
<212> TYPE: PRT
<213> ORGANISM: Medicago sativa

<400> SEQUENCE: 2

Met Ala Leu Ser Ala Ser Lys Val Ser Ile Phe Ser Pro Ser Pro Ile
1               5                   10                  15

Val Gly His Phe Ser Lys Asn Thr Thr Phe Ser Ser Leu Asn Leu Pro
                20                  25                  30

Met Asp Gly Asp Lys Arg Lys Asn Val Lys Val His Ala Ala Ala Ala
            35                  40                  45

Asn Ala Pro Thr Ala Leu Thr Gly Val Ile Phe Glu Pro Phe Glu Glu
        50                  55                  60

Val Lys Lys Asp Val Leu Ala Val Pro Ile Ala His Asn Val Ser Leu
65                  70                  75                  80

Ala Arg Gln Asn Tyr Gln Asp Glu Val Glu Ser Ala Ile Asn Glu Gln
                85                  90                  95

Ile Asn Val Glu Tyr Asn Val Ser Tyr Val Tyr His Ser Leu Phe Ala
            100                 105                 110

Tyr Phe Asp Arg Asp Asn Val Ala Leu Lys Gly Leu Ala Lys Phe Phe
        115                 120                 125

Lys Glu Ser Ser Glu Glu Glu Arg Glu His Ala Glu Lys Leu Met Lys
130                 135                 140

Tyr Gln Asn Ile Arg Gly Gly Arg Val Val Leu His Pro Ile Val Ser
145                 150                 155                 160

Pro Pro Ser Glu Phe Asp His Ala Glu Lys Gly Asp Ala Leu Tyr Ala
                165                 170                 175

Met Glu Leu Ala Leu Ser Leu Glu Lys Leu Val Asn Glu Lys Leu Leu
            180                 185                 190

Asn Val His Ser Val Ala Asp Arg Asn Asn Asp Pro Gln Leu Ala Asn
        195                 200                 205

Phe Ile Glu Ser Glu Phe Leu Val Glu Gln Val Glu Ser Ile Lys Lys
    210                 215                 220

Ile Ser Glu Tyr Val Thr Gln Leu Arg Leu Val Gly Lys Gly His Gly
225                 230                 235                 240

Val Trp His Phe Asp Gln Thr Leu Leu His
                245                 250

<210> SEQ ID NO 3
<211> LENGTH: 250
<212> TYPE: PRT
```

<213> ORGANISM: Unknown Organism
<220> FEATURE:
<223> OTHER INFORMATION: Description of Unknown Organism: we do not have
      this information

<400> SEQUENCE: 3

Met Ala Leu Ser Ala Ser Lys Val Ser Ile Phe Ser Pro Ser Pro Ile
 1               5                  10                  15

Val Gly His Phe Ser Lys Asn Thr Thr Phe Ser Ser Leu Asn Leu Pro
                20                  25                  30

Met Asp Gly Asp Lys Arg Lys Asn Val Lys Val His Ala Ala Ala Ala
            35                  40                  45

Asn Ala Pro Thr Ala Leu Thr Gly Val Ile Phe Glu Pro Phe Glu Glu
        50                  55                  60

Val Lys Lys Asp Val Leu Ala Val Pro Ile Ala His Asn Val Ser Leu
65                  70                  75                  80

Ala Arg Gln Asn Tyr Gln Asp Glu Val Glu Ser Ala Ile Asn Glu Gln
                85                  90                  95

Ile Asn Val Glu Tyr Asn Val Ser Tyr Val Tyr His Ser Leu Phe Ala
            100                 105                 110

Tyr Phe Asp Arg Asp Asn Val Ala Leu Lys Gly Leu Ala Lys Phe Phe
        115                 120                 125

Lys Glu Ser Ser Glu Glu Arg Glu His Ala Glu Lys Leu Met Lys
    130                 135                 140

Tyr Gln Asn Ile Arg Gly Gly Arg Val Val Leu His Pro Ile Val Ser
145                 150                 155                 160

Pro Pro Ser Glu Phe Asp His Ala Glu Lys Gly Asp Ala Leu Tyr Ala
                165                 170                 175

Met Glu Leu Ala Leu Ser Leu Glu Lys Leu Val Asn Glu Lys Leu Leu
            180                 185                 190

Asn Val His Ser Val Ala Asp Arg Asn Asn Asp Pro Gln Leu Ala Asn
        195                 200                 205

Phe Ile Glu Ser Glu Phe Leu Val Glu Gln Val Glu Ser Ile Lys Lys
    210                 215                 220

Ile Ser Glu Tyr Val Thr Gln Leu Arg Leu Val Gly Lys Gly His Gly
225                 230                 235                 240

Val Trp His Phe Asp Gln Thr Leu Leu His
                245                 250

<210> SEQ ID NO 4
<211> LENGTH: 27
<212> TYPE: DNA
<213> ORGANISM: Unknown Organism
<220> FEATURE:
<223> OTHER INFORMATION: Description of Unknown Organism:  Other nucleic
      acid - "synthetic oligonucleotide "

<400> SEQUENCE: 4
ccgaattcca tggctctttc agcttcc                                    27

<210> SEQ ID NO 5
<211> LENGTH: 27
<212> TYPE: DNA
<213> ORGANISM: Unknown Organism
<220> FEATURE:
<223> OTHER INFORMATION: Description of Unknown Organism:  other nucleic
      acid - "synthetic oligonucleotide"

```
<400> SEQUENCE: 5
gggaattcca tggatggtga taagagg                              27

<210> SEQ ID NO 6
<211> LENGTH: 27
<212> TYPE: DNA
<213> ORGANISM: Unknown Organism
<220> FEATURE:
<223> OTHER INFORMATION: Description of Unknown Organism: other nucleic
      acid - "syntheic oligonucleotide"

<400> SEQUENCE: 6
cggatccatg gactacaagg acgagga                              27
```

OXIDATIVE STRESS RESISTANCE GENE

This is a continuation of PCT application PCT/GB98/01108, filed Apr. 16, 1998, the entire content of which is hereby incorporated by reference in this application.

The present invention relates to plants, especially transgenic plants, plant parts and plant cells overproducing an iron binding protein (e.g. ferritin) and having an enhanced resistance against a wide range of abiotic and biotic oxidative stress conditions (e.g. against treatment with paraquat or fusaric acid and against viral, bacterial and fungal infections). The invention also comprises nucleic acid sequences encoding an alfalfa ferritin or functional variants thereof and the use of said sequences for rendering plants resistant against oxidative stress conditions.

The invention is useful for reducing environmental damages of crops caused by a wide variety of stress conditions.

With respect to the present specification and claims, we will use the following technical terms in accordance with the given definitions. With regard to the interpretation of the present invention, it shall be understood that the below defined terms are used in accordance with the given definitions even if said definitions might not be in perfect harmony with the usual interpretation of said technical term.

A "functional variant" of a protein is a polypeptide the amino acid sequence of which can be derived from the amino acid sequence of the original protein by the substitution, deletion and/or addition of one or more amino acid residue in a way that, in spite of the change in the amino acid sequence, the functional variant retains at least a part of at least one of the biological activities of the original protein that is detectable for a person skilled in the art. A functional variant is generally at least 50% homologous (i.e. the amino acid sequence of it is 50% identical), advantageously at least 70% homologous and even more advantageously at least 90% homologous to the protein from which it can be derived. Any functional part of a protein or a variant thereof is also termed functional variant.

The term "overproducing" is used herein in the most general sense possible. A special type of molecule (usually a polypeptide or an RNA) is said to be "overproduced" in a cell if it is produced at a level significantly and detectably higher (e.g. 20% higher) than natural level. Overproduction of a molecule in a cell can be achieved via both traditional mutation and selection techniques and genetic manipulation methods. The term "ectopic expression" is used herein to designate a special realisation of overproduction in the sense that, for example, an ectopically expressed protein is produced at a spatial point of a plant where it is naturally not at all (or not detectably) expressed, that is, said protein is overproduced at said point.

A plant, plant part, a plant tissue or a plant cell is said to have an "enhanced resistance" against a damaging effect, eg. damaging agent, if it can tolerate a significantly and detectably (e.g. at least 20%) stronger damaging effect, eg. dose or intensity of damaging agent, of the same type, without suffering any detectable damage, than its natural counterpart would do.

Within the framework of the present description a "ferritin protein" is defined, as it is usual in the art, as a protein capable binding iron ions (Theil E. C., 1987, Ann. Rev. Biochem. 56: 289–315). The members of the eucariotic ferritin family are highly conserved both in their amino acid sequence and three dimensional structure (Lobreaux, S. et al., 1992, Biochem. J. 288: 931–939).

The term "oxidative stress" is again used in very general sense comprising all kind of abiotic (e.g. treatment with different chemical agents or exposure to extreme weather conditions like high or low temperature or drought) and biotic (infection by different infectious agents) stress conditions in the manifestation of damaging effects of which oxidatively induced active radicals play a detectable role.

BACKGROUND OF THE INVENTION

During their different developmental stages plants are exposed to an extremely wide range of both biotic and abiotic stress conditions. It is, thus, a very important task of high economic significance to develop new breeding stocks of enhanced general stress resistance.

Under stress conditions such as high light intensity, UV-B irradiation, heavy metal contamination, high or low temperature, water deficiency, flooding, wounding, infection by viruses, bacteria, fungi, damage caused by insects and the like, oxygen toxicity can significantly contribute to the damage of crop plants. Reactive oxygen species as singlet oxygen, superoxide radical ($O_2$), hydroxyl radical ($OH^+$) and hydrogen peroxide ($H_2O_2$) play a key role in injury of stressed plants. There is good evidence that the biological damage attributed to superoxide and hydrogen peroxide is dependent on the presence of iron. The intracellular pool of free iron can react with $H_2O_2$ or $O_2^-$ giving rise to the very reactive hydroxyl radical via Haber-Wiess or Fenton reaction (Halliwell and Gutteridge, 1984, Biochem. J. 219: 1–14). Intracellularly, most of the non-metabolised iron is sequestered in ferritin; therefore ferritin is able to restrict the availability of iron and so the generation of the very reactive hydroxyl radicals. cDNAs encoding ferritin have been isolated from variety of plant species. These proteins are highly conserved both in amino acids sequence and three dimension structure (Lobreoux S. et al. 1992, Biochem. J. 288: 931–939.). Ferritins are localised in chloroplasts and iron can activate their synthesis (Seckbach, J. 1982, J. Plant. Nutr. 5: 369–394; Lobreaux et al. 1992, Plant Mol. Biol. 19: 563–575). Under normal growth conditions ferritin is synthesised only in embryo and not in vegetative organs, like roots and leaves (Lobreaux and Briat: Biochem. J. 1991, 274: 601–606).

Significant antioxidant effect of ferritin molecules can be expected in systems where ferritin synthesis and degradation is released from the normal metabolic regulation. It has been demonstrated that during oxidative stress conditions, degradation of ferritin molecules occurs and the so released iron ions highly accelerate the production rate of the damaging radical species (Cairo et al. 1995, Journal of Biochemical Chemistry 270: 700–703). Numerous traditional plant breeding and genetic manipulation approaches are known in the art for improving the resistance of specific crops against preselected desired stress conditions (e.g. against cold, drought, UV light or pathogens). These known methods, however, will not be individually detailed herein as they are all highly different from the approach of the invention. The common feature of all these previously disclosed approaches is that they enhance the resistance of different plants against a single preselected stress condition (or against a limited groups of stress conditions of the same origin) e.g. by expressing a specific resistance gene. However, no specific approach providing plants with resistance against a wide range of both abiotic and biotic stress conditions is known in the art.

SUMMARY OF THE INVENTION

It is, thus, an object of the present invention to provide a novel and general method suitable to provide crops, especially transgenic crops, with enhanced resistance against a wide range of both abiotic and biotic stress conditions.

According to another aspect, it is also an object of the invention to provide crops and breeding material, advantageously transgenic, having increased resistance against a wide range of both abiotic and biotic stress conditions.

On the basis of the foregoing disclosure it has, thus, became clear to the inventors that a substantially new genetic manipulation approach is to be developed so as to achieve the above defined objects, possibly targeting a common step in the damaging mechanism of the different abiotic and biotic stress conditions.

The approach of the present invention is, thus, based on the novel theoretical concept that overproducing or ectopically expressing ferritin or other iron binding proteins, e.g. transferring, in different organs of plants will lower the intracellular iron concentration and, therefore, reduce the damaging effects of oxygen induced free radicals. It is important to emphasise hereby that the approach of the invention is absolutely novel, as there is no method disclosed in the art that would provide plants with resistance against a wide range of both abiotic and biotic stress conditions. Furthermore, there is no approach disclosed so far according to which a ferritin protein is overproduced in plants for any reason in any manner.

Therefore, to achieve the above-defined objects of the invention we have cloned a ferritin cDNA gene from alfalfa (*Medicago sativa L.*) and overproduced it in vegetative tissues of tobacco plants.

It was found, that in accordance with the basic concept of the invention, the transgenic tobacco plants expressing the alfalfa ferritin ectopically in their vegetative tissues show significantly higher resistance towards both abiotic (treatment with different chemicals) and biotic (viral, bacterial and fungal infections) stress conditions than the starting tobacco plants and transformants show improved general adaptation and regeneration characteristics, as well.

It should be also emphasised that according to the basic concept of the invention it is probable that overproduced ferritin molecules express their general protective effect via binding free iron ions in the plant cells, it can be assumed that by overproducing other iron binding proteins, such as transferring, a similar protective effect could be achieved.

The present invention, therefore, provides plant cells overproducing an iron binding protein and having an enhanced resistance against oxidative stress. The plants of the invention are advantageously produced by genetic manipulation methods known per se but can also be produced via traditional mutation and selection techniques. The transformed plants of the invention show significantly higher resistance to oxidative stress conditions than their unmodified counterparts not expressing elevated levels of an iron binding protein.

The plant cells according to the invention are advantageously transgenic cells transformed by the introduction of a nucleic acid, eg in the form of vector, coding for the expression of an iron binding protein, advantageously ferritin.

According to preferred embodiments of the invention there are provided plant cells of the invention are overproducing a ferritin having the amino acid sequence of SEQ ID No 2 as shown in the attached sequence listing, or a functional variant thereof, said functional variant being advantageously at least 50%, more advantageously at least 70% and even more advantageously at least 90% homologous to said ferritin polypeptide.

The invention further provides plants, advantageously transgenic plants, and parts thereof comprising cells according to the invention.

According to a preferred embodiment of the invention, the intensity of the photosynthetic reactions is not decreased following a 70 hours treatment with 10 $\mu$M paraquat in the leaves of the plants of the invention.

Plant, plant parts or plant cells according to the invention advantageously have an enhanced resistance against fusaric acid treatment and/or infections of viral and/or bacterial and/or fungal origin.

The invention also provides isolated, enriched, cell free and/or recombinant nucleic acids of sequence comprising or consisting of a nucleotide sequence coding for an alfalfa ferritin having the sequence of SEQ ID No: 2, as shown in the sequence listing included herewith, and functional variants thereof. Preferably the nucleic acids have homology of at least 90% with that of SEQ ID No 1 (the DNA sequence in FIG. 1), more preferably at least 95% and most preferably at least 98%. Preferably these nucleic acids are cDNAs, recombinant vectors or other recombinant constructs.

The invention also comprises the use of these nucleic acids for the preparation of plant cells, plant parts and plants according to the invention.

The present disclosure and examples below demonstrate that synthesis of the iron binding protein ferritin in vegetative tissues of plants provides resistance against paraquat generated free radicals. In agreement with this observation we have also demonstrated a significant reduction of the symptoms after infection of the transgenic plants of the invention with a wide range of unrelated pathogens. This novel technology according to the present invention based on ectopic expression of an iron binding protein, therefore, potentially has high agronomic significance in that it may reduce primary oxidative damage in crops caused by either biotic or abiotic stress conditions. Though not wishing to be bound to any theoretical interpretation, we think that the above findings support the assumption that iron ions are more effectively bound in the plants according to the invention as a consequence of the overproduction of an iron binding protein (ferritin) and, therefore, damage caused by oxygen induced free radicals are reduced and general adaptation and regenerative properties of the plants of the invention are improved. Plants according to the invention will also be able to show resistance against other stress conditions not tested so far, e.g. against extremely low or high temperatures and drought, where such iron mediated degeneration is implicated.

Though it is considered to be quite clear from the above disclosure for a person skilled in the art, we also wish to emphasise here the universality of the approach according to the invention. We have demonstrated that ectopical expression of an iron binding protein of alfalfa origin in vegetative tissues confers resistance to transgenic tobacco plants against a wide variety of stress conditions. As the pioneering approach of the invention is based on the absolutely general concept of reducing the concentration of iron ions in the targeted tissues of plants, a person skilled in the art will understand that the advantages of the invention can not be restricted to the specific embodiments shown but this novel approach for ensuring general stress resistance to plants can be used in the case of any other crops of agronomic or horticultural significance.

It is also demonstrated that the ectopic overexpression of the embryo specific alfalfa ferritin in vegetative tissues of tobacco plants, using two different types of promoters (one of plant and the one of viral origin) is not at all damaging to the targeted tissue. It should, thus, be contemplated that any type of plant specific promoters (either constitutive or spatially and/or developmentally regulated) can be used in the invention for the overexpression of an iron binding protein in the desired plant part or tissue.

As the concentration of harmful radicals is usually the highest in the photosynthesising green tissues, these tissues are the first useful targets of the approach according to the invention. It should be understood, however, that, because of its above demonstrated highly universal basic concept, the invention is not at all limited to conferring stress resistance to green tissues, but it is also useful for making resistant all other plant parts of interest (e.g. root, stem, flower, fruit or specific parts of the foregoing) supposedly exposed to any kind of oxidative stress conditions (e.g. to infection by any type of pathogens).

BRIEF DESCRIPTION OF THE DRAWINGS

FIG. 1.

Figure 3:
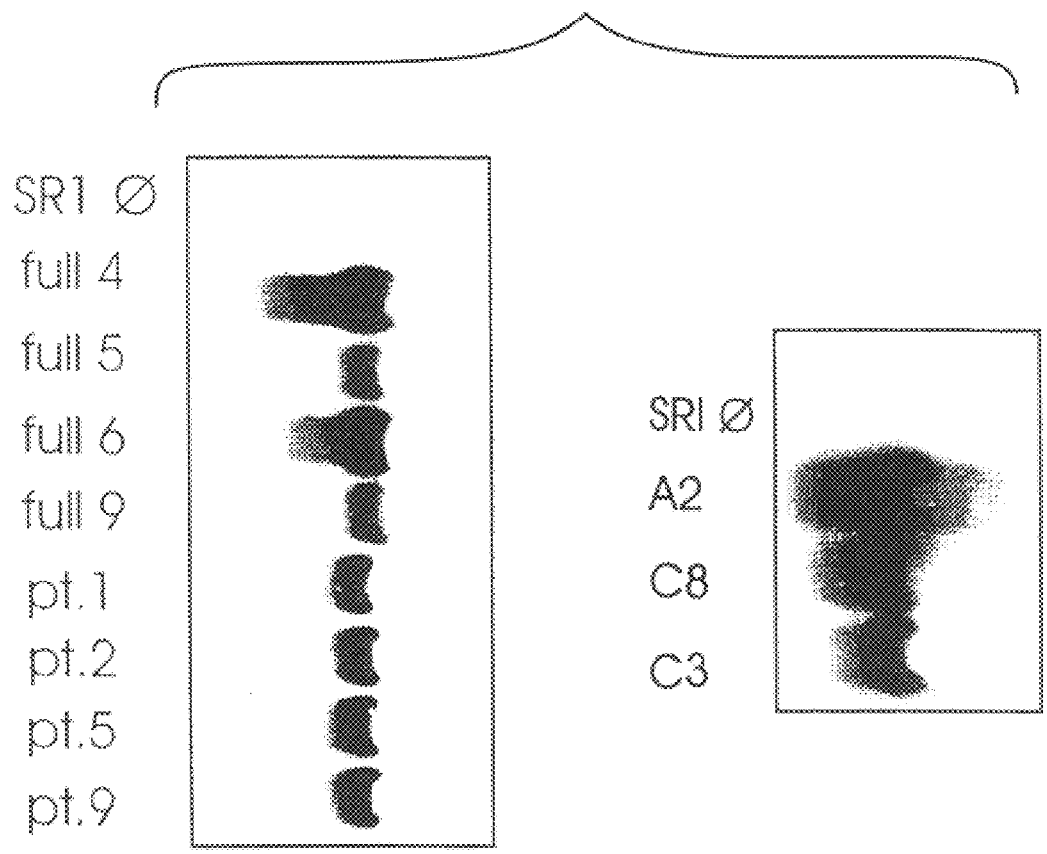

The nucleotide sequence of ferritin cDNA isolated from alfalfa (Medicago sativa) and the deduced amino acid sequence. The underlined part corresponds to the transit peptide.

FIG. 2.

Comparison of ferritin amino acid sequences from different species.

HuHfer: human H subunit (Boyd et al. 1985, J. Biol. Chem. 260: 11755)

HoLfer: horse spleen L-chain (Heuterspreute and Chrichton 1981, FEBS Lett. 129: 322)

Peafer: pea seed ferritin (Lobreoux S. et al. 1992, J. Biochem. 288: 931)

Msfer1: alfalfa ferritin (unpublished)

FIG. 3.

Accumulation of ferritin mRNAs in vegetative tissues of transgenic tobacco plants according to the invention.

FIG. 4.

Detection of ferritin in cell extract from leaves of transgenic tobacco plants according to the invention after SDS-PAGE.

FIG. 5.

Detection of ferritin in cell extract from leaves of transgenic tobacco plants according to the invention by using FLAG antibody in western blot analysis.

FIG. 6

Changes in fluorescence intensity (Fv/Fm) in leaf discs from SR1 control and C3 transformed plants of the invention during treatment with 10 $\mu$M paraquat.

FIG. 7.

Changes in fluorescence intensity (Fv/Fm) in leaf discs from SR1 control and various transformed plants according to the invention after treatment with 10 and 20 $\mu$M paraquat.

FIG. 8.

The chlorophyll content in leaves of control SR1 and transformed plants of the invention after 3 day-treatment with 10 and 20 $\mu$M paraquat.

DETAILED DESCRIPTION OF PREFERRED EMBODIMENTS AND EXAMPLES

Some preferred embodiments and the concept of the invention will be further illustrated by way of the below experimental examples. It shall be understood, however, that the examples below are presented only for more comprehensive understanding of the spirit of the invention and are no way illustrative or limiting as to the scope of the invention, which is, in turn, defined in the attached claims.

In the below examples, we demonstrate numerous advantages of the of the invention as reduced to practice. We have isolated a full length cDNA clone (MsFER1) encoding a novel alfalfa ferritin polypeptide and used this cDNA for the expression of ferritin in vegetative tissues of transgenic tobacco plants under the transcriptional control of different promoters. After biochemically characterising the ferritin expressing transgenic tobacco plants, we have demonstrated that most of them have a significantly enhanced resistance against different abiotic (treatment with damaging chemical agents) and biotic (infections with viral, bacterial and fungal pathogens) stress conditions of very different origin.

EXAMPLE 1

Identifying a Full Length Alfalfa Ferritin cDNA (MsFER1) Clone and Determining the Nucleic Acid and Deduced Amino Acid Sequence Thereof For constructing a cDNA library and isolating the cDNA clone coding for ferritin, the usual methods of recombinant DNA technology were used as described in "Molecular cloning, A Laboratory Manual" (2. edition, Cold Spring Harbour N.Y, 1989) by Sambrook J., Fritsch, F. F. and Maniatis T.

Specifically, the alfalfa ferritin cDNA clone was isolated as follows.

Total cellular RNA was isolated from in vitro cultured alfalfa tissues primarily consisting of somatic embryos. Small amounts of callus tissues were also present in the samples (Cathala et al. 1983, DNA, 2: 329–335). The formation of somatic embryos was induced by applying auxin (2,4 dichlorophenoxyacetic acid) shock as described by Dudits et al. (1991, J. Cell Science, 99: 473–482.).

Then, mRNA was purified from the total cellular RNA isolate by oligo-dT cellulose chomatography (Aviv H. and Leder P. 1972, Proc. Natl. Acad. Sci. USA 69: 1408–1412.).

First strand cDNA was then synthesised with AMV reverse transcriptase in the presence of oligo dT primer. The second strand was produced by DNA polymerase I. After RNase H treatment, cDNA was annealed into a PstI digested pGEM2 vector (Promega) after dC and dG homolinker addition with terminal transferase. The products were transformed into E. coli MC 1061 strain and selected by 100 mg/l ampicillin. 2.5×10$^5$ primary transformants were produced by using 25 $\mu$g cDNA. Ninety-six percent of the clones comprised a cDNA insert of significant size. The procedure is described in detail by De Loose et al. (1988, Gene 70: 13–23).

Fifty ESTs were then identified by randomly sequencing preselected cDNA clones. Pharmacia T7 Sequencing Kit or USB Sequenase 2.0 kit were used for sequencing according to the instructions of the manufacturer. Preselection was done by Northern hybridising the cDNA clones with an RNA probe prepared from somatic embryos. Strongly hybridising clones were selected.

Sequence alignment based on GenBank and EMBL data bank revealed one cDNA clone (designated as MsFER1) with high homology to the known ferritins at the deduced amino acid sequence. FIG. 1 presents both nucleotide (SEQ ID NO: 1) and amino acid sequence (SEQ ID NO: 2) of the MsFER1 clone. The cDNA insert comprised in this clone is 1036 bp long and the coding region is found between positions 40 and 789. The encoded protein is composed by 251 amino acids and it shares high amino acid sequence identity with ferritins of different origin. As shown in FIG. 2, plant ferritins share 39–49% amino acid identity with the human H and the horse L ferritins, while the sequences of the pea and the alfalfa ferritins are very similar to each other (89% of amino acid identity) in the mature protein. The two plant ferritins, however, significantly differ in their regions corresponding to the chloroplasts leader sequence. Here the identity is only 47 % in the amino acid sequence. Therefore, the newly described alfalfa ferritin can be considered as a novel variant in the ferritin family.

EXAMPLE 2

Introduction of the Alfalfa Ferritin cDNA into Tobacco Plants for Ectopic Expression of this Protein in Vegetative Tissues The applied transformation technology is based on the Agrobacterium gene delivery system reviewed by Hinchee et al. "Plant Cell and Tissue Culture" pp. 231–270, eds. I. K. Vasil T. A Thorpe, Kluwer Academic Publisher 1994. In the present Examples we have used the system with vectors described by Pellegrineschi et al. (1995, Biochemical Society Transitions 23: 247–250).

The MsFER1 cDNA was cloned into the BamHI/Kpnl sites of the transformation vector where it was functionally attached to the promoter of the small subunit gene of is ribulose 1.5-bisphosphate carboxylase. This promoter is originally described by Mauer and Chui (1985, Nucleic Acid Res. 7: 2373–2387) and is especially useful for expression in the green tissues of plants. The transgenic clones obtained after transforming tobacco plants named as A2, C3 and C8 carry this construct. Alternatively, the MsFER1 cDNA was also linked to the viral promoter CaMV35S described by Benfey et al. (1989, The EMBO J. 8: 2195–2202). For cloning the full length construct we used the following PCR primer synthesised in a Per Septives automated DNS synthesiser.

CCG AAT TCC ATG GCT CTT TCA GCT TCC (SEQ ID NO: 3)

Eco RI site coding region of the ferritin transit peptide

We have also generated a truncated version of MsFER1 cDNA that lacks a significant part of the targeting leader sequence (see FIG. 1). In this cloning procedure we used the following PCR primer:

GGG AAT TCC ATG GAT GGT GAT AAG AGG (SEQ ID NO: 4)

Eco RI site coding region within the transit peptide

The above mentioned oligonucleotides and T7 sequencing primer (Boehringer Mannheim) were used for PCR amplification of the defined DNA fragments (Mullis and Faloona 1987, Meth. Enzymol. 155: 335).

The EcoRI/KpnI digested PCR products (the KpnI restriction site originates from the T7 primer sequence) were cloned into the pFLAG-ATS vector (Scientific Imaging System Kodak, USA) digested with the same restriction enzymes. The presence of the FLAG sequence in these constructs enables the immunological tracking of the protein synthesis by using the Anti Flag M2 antibody (Scientific Imaging System Kodak, USA).

For generating full FLAG FERR and partial (pt) FLAG FERR constructs we synthesised the following Bam-Flag oligonucleotide:

CGG ATC CAT GGA CTA CAA GGA CGA GGA (SEQ ID NO: 5)

BamHI site MET FLAG coding sequence

Using this primer and the C24 sequencing primer of the pFLAG vector PCR products were produced and cloned into the transformation vector at BamHI/KpnI sites.

The so constructed binary vectors were mobilised into an Agrobacterium strain. Tobacco leaf discs were then co-cultured with the Agrobacterium cells and transformants were selected on kanamycin containing medium as described by Claes et al. (1991. The Plant Journal 1: 15–26). Primary transformants were self-pollinated and T2 plants were further characterised.

EXAMPLE 3

Molecular Evidence for Ectopic Synthesis of Ferritin in Transgenic Tobacco Plants Northern blot hybridisation was firstly used to show the functional activity of the introduced constructs. Northern hybridisation was done according to the widely used protocols (Sambrook J., Fritsch F. F. and Maniatis T.: "Molecular cloning, A Laboratory Manual" 2. edition, Cold Spring Harbour N.Y., 1989). First, total RNA samples were isolated from the vegetative tissues of the transformants (see Cathala et al. 1983, DNA 2: 329–335). After agarose gel electrophoresis in formaldehyde, RNA was transferred onto Hybond-N filters (Amersham, Inc.). Radiolabelled probes were generated by random-primed $^{32}$P-labelling (Freinberg A. P. and Vogelstein B. 1983. Anal. Biochem. 137: 266–267). After 4–12 hours of prehybridisation in the presence of formaldehyde, the hybridisation was carried out at 42° C. for 16–24 hours. Washing conditions were as follows: 65–72° C., 0.1×SSC, 0.1% SDS. As shown on FIG. 3, significant amounts of ferritin mRNA accumulated in the transformed plants.

Figure 4:
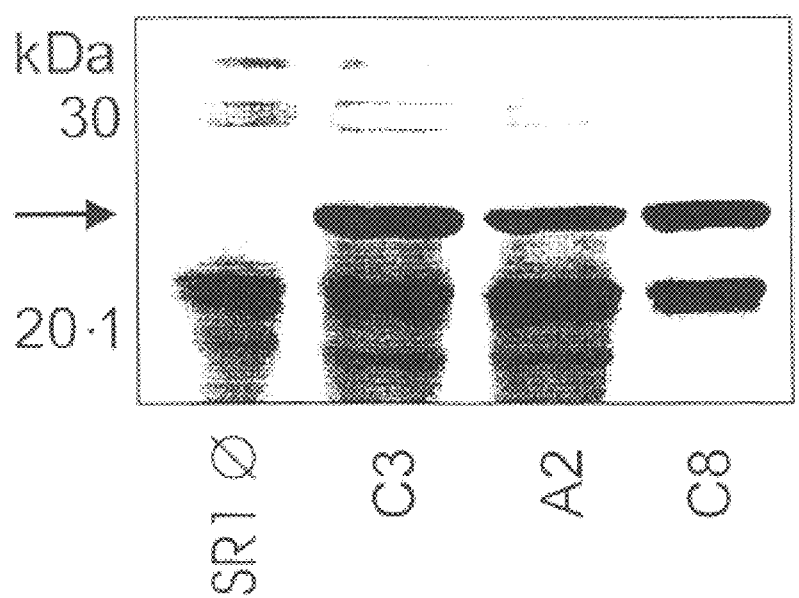
Figure 5:
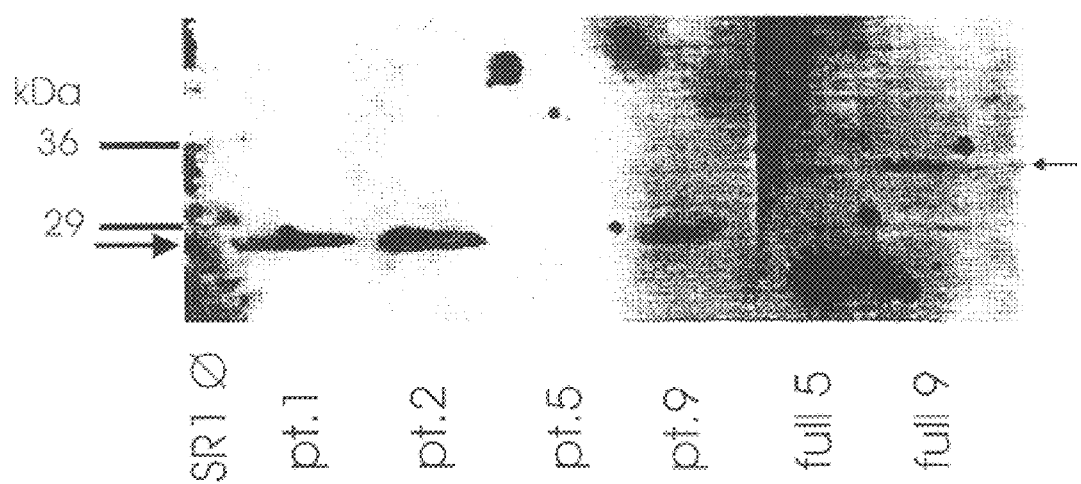

Synthesis of ferritin was analysed by biochemical methods after partial purification as described by Laulhere and Laulhere (1989, J. Biol. Chem. 264: 3629–3635). After SDS-PAGE, the protein profiles of the control SR1 plants and the transformants (C3, A2, C8) differed significantly. The later ones accumulated variable amounts of ferritin having a molecular mass of 26 kDa (FIG. 4). Using the FLAG detection system we could also show the synthesis of ferritin by chemiluminescence (Super Sigfnal$^{RM}$-CL-HRP System, Pierce) in several transgenic tobacco plants (FIG. 5). The presented molecular data convincingly show the lack of ferritin in the control plants and accumulation of this protein in vegetative tissues of the transformants.

EXAMPLE 4

Ectopic Synthesis of Ferritin Provides Oxidative Stress Resistance for Transgenic Plants To test the basic concept of this invention we have analysed the paraquat (Pq) resistance of control and transformed tobacco plants. It is well documented that electrons produced during photosynthetic electron transport reduce Pq and free radicals are formed (Ashton F. M. and Crafts A. S. 1981, Mode of action of herbicides, Wiley, New York). Leaf discs from control and transformed plants were exposed to 10 or 20 $\mu$M Pq.

Figure 6:
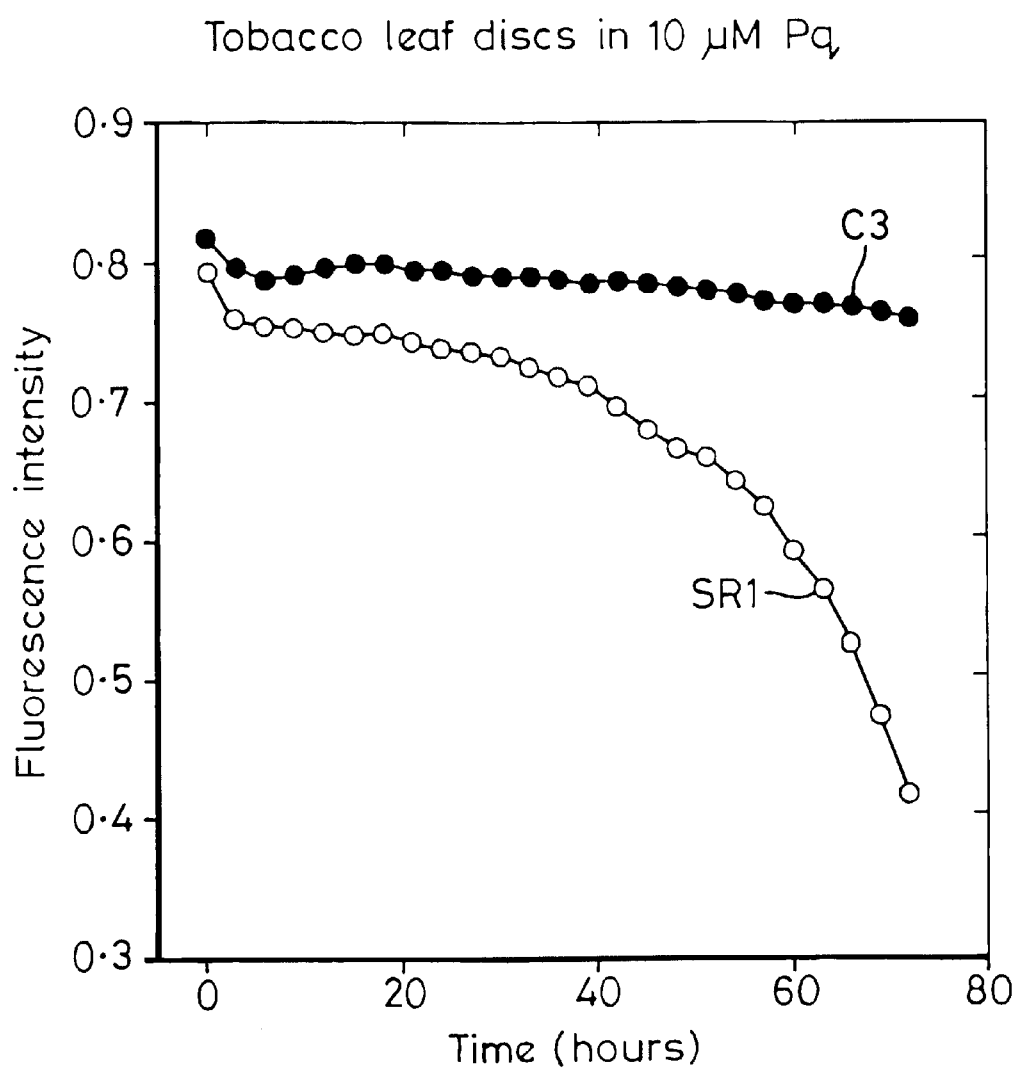
Figure 7:
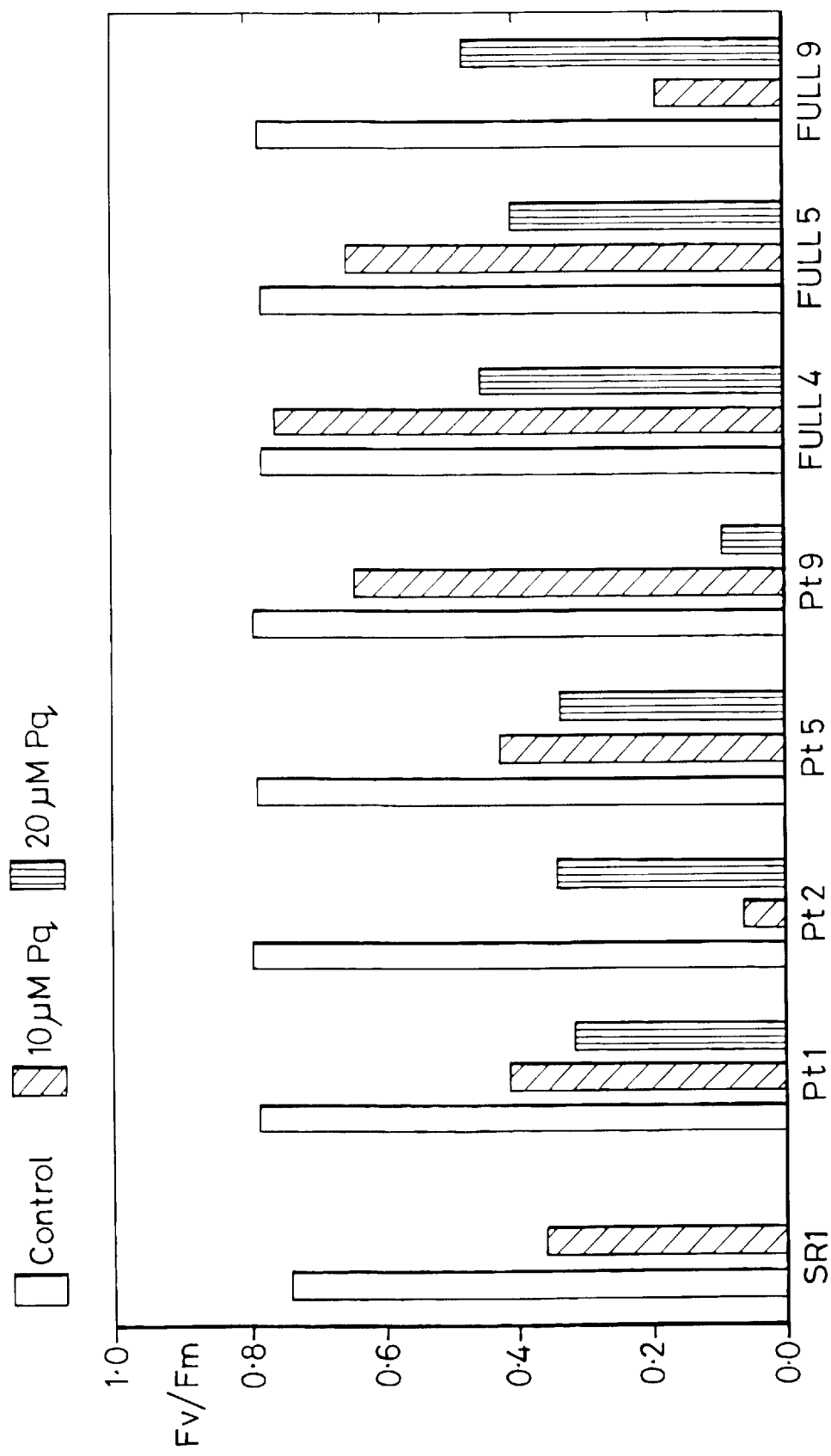
Figure 8:
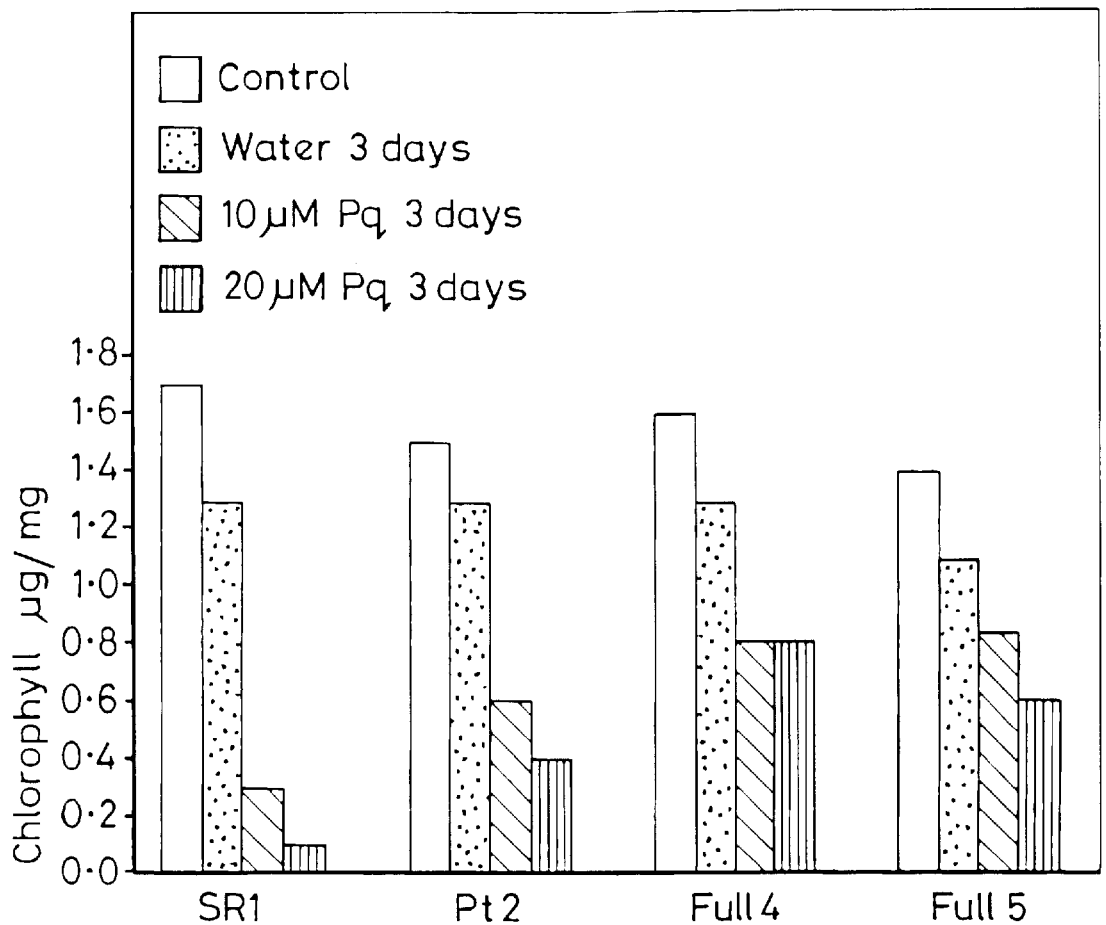

Functional damage was monitored by measuring the light activated fluorescence with PAM fluorimeter as described by Vass I. et al. (1996. Biochemistry, 35: 8964–8973). As an example, FIG. 6 shows the loss of photosynthetic function in the control SR1 leaves after 60 hours of 10 $\mu$M Pq treatment, while the C3 transformant retained its photosynthetic activity during the period analysed. Similar responses can be observed after Pq treatment of two other transformants (Full9, Pt2) in which the ferritin gene is expressed under the control of the CaMV35S promoter. These experiments were repeated several times (see also FIG. 7) and the functional characterisation convincingly proved the paraquat-resistance in the case of the transformants. This resistance can also be seen when the changes in chlorophyll contents are monitored (FIG. 8).

Using Pq as the inducer of free radicals, the presented results support the conclusion that transformed plants synthesising ferritin in their vegetative tissues express elevated tolerance against damage caused by free radicals. Here we have to mention that the analysed transformed plants lack any visible alterations during their growth under greenhouse conditions. The photosynthetic function of transformants is similar to the control SR1 plants. Under control conditions these plants exhibit normal chlorophyll content (FIG. 8).

EXAMPLE 5

Transformed Plants Overproducing Ferritin have Enhanced Resistance Against Fusaric Acid Treatment The involvement of free radicals in pathogenicity has been proposed by K. E. Hammond-Kosack and J. D. G. Jones (1996, The Plant Cell 8: 1773–1791). Therefore, we have tested the development of symptoms on transformants expressing the alfalfa ferritin gene in green tissues. First, we analysed the effects of fusaric acid as a non-specific fungal toxin. Fusaric acid in different concentrations was injected into control (SR1) and transgenic (A2, C3 and C8) tobacco leaves. 2 days after injection we analysed the degree of necrotization on leaf tissues. Table 1 summarises the results of 3 experiments.

TABLE 1

Reduced necrotization in transformed plants expressing ferritin after fusaric acid treatment

|     | $2.5 \times 10^{-3}$ M | | $1.25 \times 10^{-3}$ M | | $2.5\ 10^{-3}$ M | |
| --- | --- | --- | --- | --- | --- | --- |
| SR1 | XXX | (100%) | XX(X) | (73%) | XXX | (100%) |
| A2  | X   | (28%)  | -(X)  | (16.5%) | X(X) | (50%) |
| C3  | X   | (65%)  | -(X)  | (16.5%) | X(X) | (50%) |
| C8  | X   | (70%)  | X(X)  | (50%)  | XX  | (73.5%) |

– no necrotization; XXX = severe necrotization (or % of necrotization of the injected leaf area)

The presented data show considerable reduction of necrotization on the leaves of the transformed plants. These results also promise enhanced resistance against damages caused by fungal infections.

EXAMPLE 6

Transformed Plants Overproducing Ferritin have Enhanced Resistance Against Pseudomonas Infection Along the same concept, we have injected *Pseudomonas syringae* bacterium suspension ($10^7$/ml) into the leaves of tobacco plants. After 20 hours, the degree of necrotization (HR) were analysed. Table 2. summarises the results indicating reduced necrosis in two transgenic lines (A2, C8).

TABLE 2

The degree of necrotization after bacterial infection

|     | Exp. A | Exp. B |
| --- | --- | --- |
| SR1 | 100% | 100% full necrosis |
| A2  | 20%  | 30% |
| C3  | 100% | 100% |
| C8  | 30%  | 35% |

The above data demonstrates that at least two of the transformants (A2 and C8) have a significantly enhanced resistance against the damages caused by bacterial infection.

EXAMPLE 7

Transformed Plants Overproducing Ferritin have Enhanced Resistance Against Botrytis and Alternaria Fungal Infection We have tested the response of transgenic lines according to Ex. 2 against two fungal pathogens such as *Alternaria alternata* and *Botrytis cinerea*. Leaves were detached and inoculated with agar block (5 mm diam) from the fungal culture. Table 3 summarises the sizes of necrotised leaf areas of the treated control and transformant plants.

TABLE 3

Effect of fungal pathogens on transformed plants

| | *Alternaria alternata* | | *Botrytis cinerea* | |
| --- | --- | --- | --- | --- |
| Tobacco | mm$^2$ | % | mm$^2$ | % |
| SR1 | 723.4 ± 224.0 | 100.0 | 516.9 ± 118.4 | 100.0 |
| A2  | 204.1 ± 50.2  | 28.2  | 278.3 ± 101.6 | 53.8  |
| C3  | 286.5 ± 59.6  | 39.6  | 56.9 ± 6.7    | 11.0  |
| C8  | 198.2 ± 85.2  | 27.4  | 290.5 ± 89.5  | 56.2  |
| PT1 | 543.2 ± 163.2 | 75.1  | 497.7 ± 117.7 | 96.3  |
| PT2 | 407.0 ± 123.6 | 56.3  | 334.8 ± 80.4  | 64.8  |
| PT5 | 520.1 ± 140.1 | 71.9  | 257.5 ± 56.5  | 49.8  |
| Full4 | 268.9 ± 14.5 | 37.2 | 317.1 ± 62.8  | 61.3  |
| Full5 | 435.0 ± 55.3 | 60.1 | 476.1 ± 96.1  | 92.1  |
| Full9 | 113.4 ± 63.0 | 15.7 | 278.3 ± 101.6 | 53.8  |

From the above data, one can conclude that the transformed tobacco plants—comprising either the full or the truncated version of the ferritin gene—expressing ferritin in their leaves show significantly reduced symptoms (though in variable degree) in comparison with control plants.

EXAMPLE 8

Transformed Plants Overproducing Ferritin have Enhanced Resistance against Tobacco Necrotic Virus (TNV) Infection In the infection of plants with viruses oxygen generation plays an essential role in pathogenicity. Therefore we have tested the responses of the transformed and control (SR1) plant against tobacco necrotic virus (TNV) infection (Table 4).

TABLE 4

Reduction of number and area of lesion in transformed tobacco plants after TNV infection

| Experiment 1 | | |
| --- | --- | --- |
| SR1 (control) | 17.4 ± 2.5 | (total lesion, cm$^2$) |
| C3 (transformant) | 6.4 ± 1.4 | |
| C8 (transformant) | 6.5 ± 1.2 | |
| A2 (transformant) | 6.1 ± 1.7 | |
| Experiment 2 | | |
| SR1 (control) | 50.0 ± 10.0 | (number of lesions) |
|  | 35.8 ± 21.7 | |
| Pt1 (transformant) | 25.8 ± 7.3 | |
| Pt2 (transformant) | 12.5 ± 8.4 | |
| Pt5 (transformant) | 18.7 ± 12.3 | |
| Pt9 (transformant) | 38.3 ± 8.6 | |
| Full4 (transformant) | 45.0 ± 19.1 | |
| Full5 (transformant) | 32.0 ± 16.8 | |
| Full6 (transformant) | 46.2 ± 6.1 | |
| Full9 (transformant) | 21.7 ± 13.7 | |

As shown in Table 4, significant reduction in number of lesions can be recognised in transformed tobacco lines carrying the alfalfa ferritin gene under the control of promoter from small subunit of RUBISCO (C3, C8 and A2). It might have a functional significance that among the transformed lines expressing the ferritin gene under the control of the CaMV35S promoter, two lines expressing the truncated ferritin gene showed the most significant reduction in the symptoms.

What is claimed is:

1. A method for producing a transformed plant cell, plant or plant part which expresses iron binding ferritin protein, comprising transforming a plant cell, plant or plant part with a nucleotide sequence encoding an iron binding ferritin protein of SEQ ID NO:2, and expressing said protein, wherein the level of ferritin in the transformed plant cell, plant or plant part is higher than that of an untransformed cell, plant or plant part.

2. The method as claimed in claim 1, wherein the transformed plant cell, plant or plant part is resistant to an oxidative stress.

3. The method as claimed in claim 2, wherein the oxidative stress is induced by free radicals or by pathogenic infections.

4. A method for producing a transformed plant cell, plant or plant part which expresses a polypeptide having iron binding ferritin activity, comprising transforming a plant cell, plant or plant part with a nucleotide sequence encoding a polypeptide having at least 90% sequence identity with SEQ ID NO:2, wherein the encoded polypeptide retains iron binding ferritin activity, and expressing said polypeptide, wherein the level of the iron binding ferritin polypeptide in the transformed plant cell, plant or plant part is higher than that of an untransformed cell, plant or plant part.

5. The method as claimed in claim 4, wherein the transformed plant cell, plant or plant part is resistant to an oxidative stress.

6. The method as claimed in claim 5, wherein the oxidative stress is induced by free radicals or by pathogenic infections.

7. A method for producing a plant which is resistant to an oxidative stress, comprising transforming a plant cell with a nucleotide sequence encoding an iron binding ferritin protein of SEQ ID NO:2, regenerating a plant from the transformed plant cell, and expressing said protein, wherein the level of ferritin in the transformed plant is higher than that of an untransformed plant, and whereby the transformed plant is resistant to an oxidative stress.

8. The method as claimed in claim 7, wherein the transformed plant exhibits reduced loss of photosynthetic function and necrotization as compared to an untransformed counterpart plant under oxidative stress conditions.

9. A method for producing a plant which is resistant to an oxidative stress, comprising transforming a plant cell with a nucleotide sequence encoding a polypeptide having at least 90% sequence identity with SEQ ID NO:2, wherein the encoded polypeptide retains iron binding ferritin activity, regenerating a plant from the transformed plant cell, and expressing said polypeptide, wherein the level of ferritin in the transformed plant is higher than that of an untransformed plant, and whereby the transformed plant is resistant to an oxidative stress.

10. The method as claimed in claim 9, wherein the transformed plant exhibits reduced loss of photosynthetic function and necrotization as compared to an untransformed counterpart plant under oxidative stress conditions.

11. The method as claimed in claim 4 or 9, wherein the nucleotide sequence encoding said polypeptide has at least 90% sequence identity to SEQ ID NO:1.

* * * * *